United States Patent [19]

Le Compagnon et al.

[11] Patent Number: 5,033,308
[45] Date of Patent: Jul. 23, 1991

[54] METHOD AND APPARATUS FOR TESTING CHARACTERISTICS OF EXTRUDED ELASTOMERIC WEATHERSTRIPS

[75] Inventors: Gilles Le Compagnon, Dover; David A. Ross, Amherst, both of N.H.

[73] Assignees: Harvard Industries; The Kingston-Warren Corporation, both of Newfields, N.H.

[21] Appl. No.: 544,400

[22] Filed: Jun. 27, 1990

[51] Int. Cl.$^5$ .............................................. G01N 3/00
[52] U.S. Cl. .................................................. 73/788
[58] Field of Search ................. 73/794, 795, 823, 849, 73/860, 787–791, 818, 866, 865.9

[56] References Cited

U.S. PATENT DOCUMENTS

| | | | |
|---|---|---|---|
| 2,283,730 | 5/1942 | Gardner | 73/849 |
| 2,482,147 | 9/1949 | Bashore | 73/823 |
| 2,637,203 | 5/1953 | Gehman | 73/823 |
| 2,691,886 | 10/1954 | Cole | 73/823 |
| 3,167,964 | 2/1965 | Dega et al. | 73/865.9 |
| 4,383,450 | 5/1983 | Pringiers et al. | 73/790 |
| 4,807,397 | 2/1989 | Doan | 49/383 |
| 4,860,588 | 8/1989 | St Angelo et al. | 73/849 |
| 4,901,581 | 2/1990 | Fain et al. | 73/795 |

FOREIGN PATENT DOCUMENTS 0045530 2/1988 Japan ..................... 73/849

OTHER PUBLICATIONS

Knoepfler, "Test Methods for Evaluating Cotton Flote, a new Cotton Batting Product", Bedding Mag, Aug. 1965.

Primary Examiner—Robert Raevis
Attorney, Agent, or Firm—Lahive & Cockfield

[57] ABSTRACT

Method and apparatuses are disclosed for testing various characteristics of an elastomeric weatherstrip such as seal load, stress relaxation, and the recovery rate. One embodiment of the invention is an apparatus including a member defining a surface for exerting a force to deflect a portion of the weatherstrip a selected distance. The surface is oriented to be parallel to an edge defined by the portion along the weatherstrip's longitudinal axis in order to ensure that the exerted force is evenly distributed. The apparatus further includes an adjustable support for positioning the weatherstrip with respect to the surface and for bringing the edge into contact with the surface sufficiently to cause the portion to deflect the selected distance. The apparatus also includes a device for measuring the force exerted during deflection on the surface by the portion of the weatherstrip. Another embodiment of the invention includes a device for continually monitoring the force exerted on the surface by the portion over an extended period of deflection. The force measuring device can include a plurality of force measuring devices for independently measuring horizontal and vertical components of the exerted force. The methods of the invention include steps of exerting a force on the portion of the weatherstrip in order to deflect the portion a selected distance and measuring the reactive force exerted by the deflected portion. In another embodiment, the method includes the step of continually monitoring the measured force to determine the rate at which the portion relaxes over a period of time. Another embodiment of the method of the invention includes the steps of removing the deflective force from the portion of the weatherstrip and measuring the position of the weatherstrip at specified intervals to determine the rate at which a portion of the weatherstrip returns to its undeflected position.

22 Claims, 16 Drawing Sheets

METHOD AND APPARATUS FOR TESTING CHARACTERISTICS OF EXTRUDED ELASTOMERIC WEATHERSTRIPS

BACKGROUND OF THE INVENTION

The present invention relates generally to the field of methods and apparatuses for testing characteristics of elastomeric weatherstrips. In particular, the invention is concerned with a method and apparatus for testing seal load, relaxation rate, and recovery rate of extruded elastomeric weatherstrips.

Extruded elastomeric weatherstrips are commonly used to provide sealing between the edges of openings of motor vehicle bodies and closure elements for those openings. These weatherstrips provide protection from air, dust, and water passing through door, trunk, and window seals. To perform effectively, the weatherstrips must be manufactured to given specifications.

An elastomeric weatherstrip typically includes a first section for securing the weatherstrip to an edge of an opening in a motor vehicle body or a closure element for that opening and a second section, such as a wing, or bulb for providing sealing therebetween. An important characteristic of an elastomeric weatherstrip is the amount of force that is required to deflect the wing or bulb of the weatherstrip a selected distance. The selected distance typically corresponds to the distance that the wing or bulb will be deflected when the weatherstrip is in use. The amount of force required to so deflect the weatherstrip is typically referred to as "seal load." Ideally, a weatherstrip should have a seal load which is low enough to prevent the need for excessive force to close a window, trunk, door, or the like, while high enough to maintain effective sealing in the sealed seam.

Another important characteristic of an elastomeric weatherstrip is stress relaxation, which is the decrease in stress over time at a constant deformation. Stress relaxation is important in engineering applications because it can cause the applied seal force to become unacceptably low during operation. The force generated by a deflected weatherstrip having a high stress relaxation will decrease quickly and will result in inferior sealing in the seam in which the thus relaxed weatherstrip is positioned.

A third characteristic of an elastomeric weatherstrip is seal recovery. Seal recovery refers to the rate at which a deflected portion of a weatherstrip returns to its predeflection condition after the deflecting force has been removed. For purposes of providing effective sealing, a high seal recovery rate is desirable.

There is presently in the industry a felt need for economical and reliable measurement of the above-discussed characteristics of an extruded elastomeric weatherstrip. As a result, weatherstrips at times are manufactured without these characteristics having been monitored either adequately or at all. Accordingly, while relatively minor mechanical adjustments to the manufacturing process can improve weatherstrip quality, if that quality is not monitored the adjustments are not made and inferior weatherstrips are produced.

It is, therefore, an object of the present invention to provide an apparatus for economically and reliably measuring the above-discussed characteristics of an extruded elastomeric weatherstrip. It is a further object of the present invention to provide a method for measuring these characteristics which provides accurate data and is simple to implement. Yet another object of the present invention is to enable a superior weatherstrip to be manufactured by affording manufacturers the ability to easily monitor important characteristics of weatherstrips.

SUMMARY OF THE INVENTION

The problems associated with known methods and apparatuses for testing characteristics of elastomeric weatherstrips are greatly relieved by the present invention which allows accurate data relating to important characteristics of elastomeric weatherstrips to be easily obtained. By providing this data simply and economically, the present invention encourages the manufacture of high quality weatherstrips having improved sealing capabilities.

In one aspect, the invention includes an apparatus for measuring the seal load required to deflect a portion, such as a wing or bulb, of the profile of an elastomeric weatherstrip. The apparatus includes a plate mounted on a bearing and defining a deflecting surface, which is typically planar, for exerting a force to deflect the portion. To insure that the exerted force is evenly distributed along the portion, the deflecting surface is parallel to an edge which is defined by the portion along the weatherstrip's longitudinal axis. The invention further includes an adjustable support structure for supporting and positioning a section of the weatherstrip with respect to the deflecting surface. The support structure can be adjusted to bring the edge of the portion of the weatherstrip to be deflected into contact with the deflecting surface to an extent sufficient to cause the portion to be deflected a selected distance. A force measuring device, such as a load cell, is arranged in communication with the deflecting plate for measuring components of the force exerted during deflection on the plate by the wing or bulb of the weatherstrip.

One embodiment of the invention includes both horizontally and vertically mounted load cells. This enables the total force exerted by the portion on the deflecting surface to be broken down into vertical and horizontal components.

In another aspect, the invention includes an apparatus for determining stress relaxation during deflection of a portion, such as a wing or bulb, of the profile of an elastomeric weatherstrip. In addition to the above-described elements, this aspect of the invention includes a device for continually monitoring the force exerted by the deflected wing or bulb on the deflecting surface of the plate to determine the rate at which that force decreases. As with the above-described embodiment of the invention, by optionally providing vertically and/or horizontally mounted load cells, this embodiment of the invention allows both the vertical and horizontal components of stress relaxation to be determined.

In still another aspect, the invention includes an apparatus for determining seal recovery. In this aspect, the invention includes horizontal and vertical positioning devices which provide information relating to the position of a portion, such as a wing or bulb, of the profile of an elastomeric weatherstrip. The apparatus allows a wing or bulb of a weatherstrip to be deflected and then released and affords a user the ability to track the wing or bulb after it is released to determine the rate at which it returns to its original position.

In yet another aspect, the invention includes a method for measuring the force required to deflect a portion, such as a wing or bulb, of an elastomeric weatherstrip a selectable distance. In accordance with the method, a force is exerted on the portion using a plate mounted on a bearing, such as that described above, which defines a deflecting surface which is parallel to an edge defined by the portion along the weatherstrip's longitudinal axis. As mentioned previously, this insures that the force exerted by the plate on the portion is evenly distributed. By measuring the force exerted on the plate by the deflected portion, the force required to deflect the portion a selectable distance can be determined. In one embodiment, the step of exerting a force on the portion includes the substeps of mounting the weatherstrip on a support structure, orienting the structure so that the edge is parallel to the deflecting surface, and adjusting the support structure to bring the edge into contact with the deflecting surface of the plate to an extent sufficient to cause the portion to deflect the selected distance. In another embodiment of the invention, the method further includes the steps of separately measuring the horizontal and vertical components of the force exerted during deflection by the wing portion on the deflecting surface.

In yet another aspect, the invention includes a method for measuring the relaxation rate of a portion such as a wing or bulb, of an elastomeric weatherstrip when the portion is deflected a selectable distance. In addition to those steps described above, the method includes the step of continually monitoring the measured force to determine the rate at which the force exerted by the deflected portion on the deflecting surface relaxes over a period of time. The horizontal and vertical components of this force can be separately measured.

In still another aspect, the invention includes a method for determining the seal recovery rate, after a deflecting force has been removed, of a portion, such as a wing or bulb, of a weatherstrip. This aspect includes the steps of deflecting the wing or bulb of the weatherstrip a selected distance for a predetermined period of time. To measure the seal recovery rate, the deflecting force is removed and the position of the wing or bulb is measured at set intervals of time to determine the rate at which the wing or bulb returns to its undeflected position.

These and other aspects of the invention will be more fully understood by reference to the following detailed description in conjunction with the attached drawing in which like reference numbers refer to like members throughout the several views.

DETAILED DESCRIPTION

One aspect the invention teaches an apparatus for measuring the force required to deflect a portion, such as a wing or bulb, of an elastomeric weatherstrip a selectable distance. The invention includes a structure for supporting a section of the weatherstrip, a plate for deflecting a wing or bulb of the weatherstrip, and a device for determining the force exerted on the plate by the deflected wing or bulb.

Figure 1:
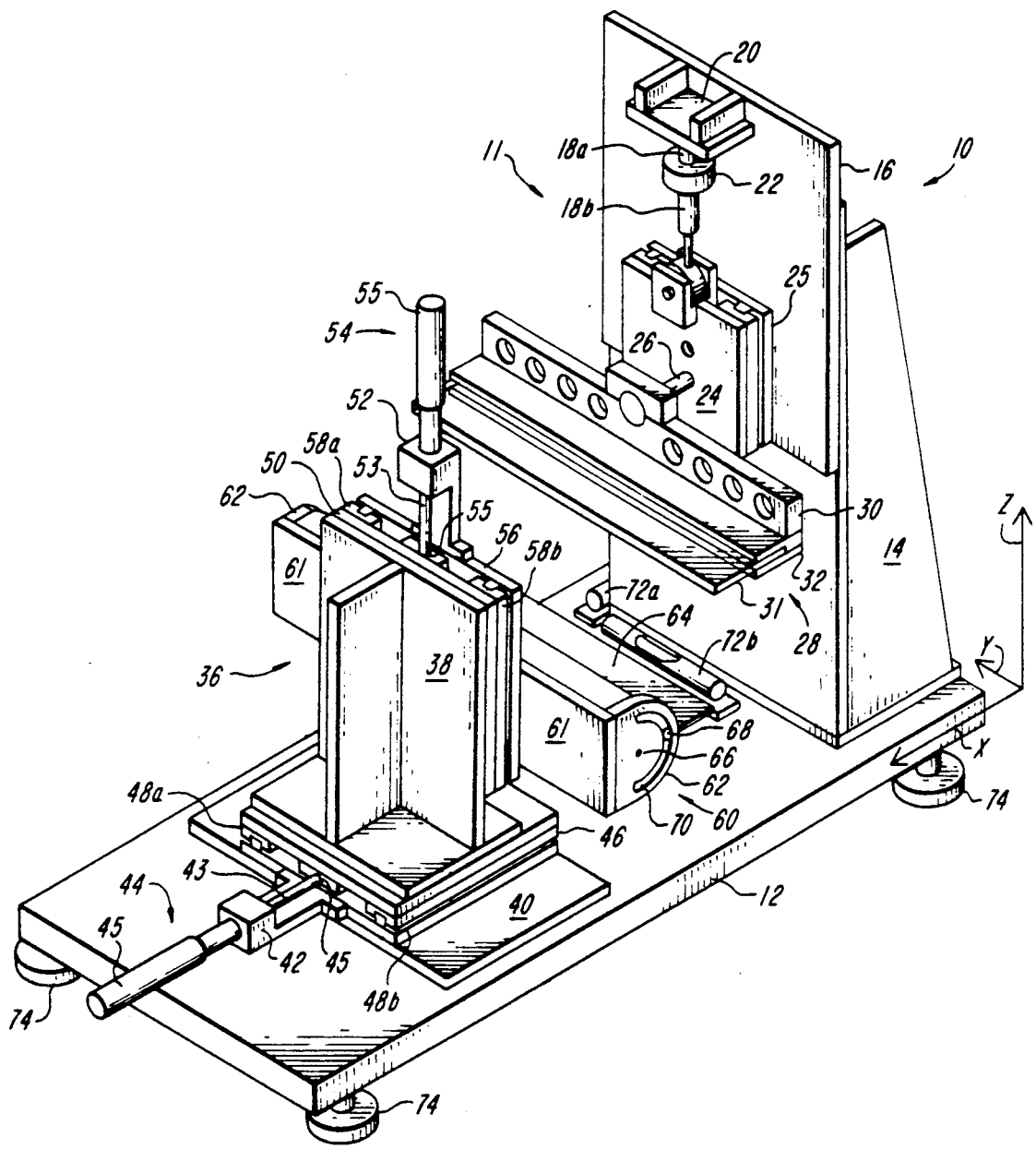
FIG. 1 is a perspective view of an apparatus constructed in accordance with the present invention.

FIG. 1 is an illustrative embodiment of an apparatus 10 constructed in accordance with the present invention. Apparatus 10 includes a horizontal base plate 12 which supports a vertical stand 14. A vertical mounting plate 16 is attached to vertical stand 14 at a selectable elevation. At the top of vertical mounting plate 16 is a vertical force measuring assembly 11 which includes a load cell anchor 20. A load cell mount 18a is connected to the bottom of anchor 20. The load cell mount 18a supports a load cell 22 which is connected, via a coupling 18b to a vertical frictionless slide 24. The frictionless slide 24 is able to reciprocate with respect to a plate 25, the latter of which is rigidly affixed to vertical mounting plate 16.

To prevent insulating load cell 22 from force exerted on frictionless slide 24, the vertical frictionless slide 24 should have an extremely small coefficient of friction with respect to the plate 25. This coefficient of friction is preferably approximately 0.003. As a result, the vertical component of any force applied to vertical frictionless slide 24 will be truly transmitted to load cell 22 via coupling 18b.

A deflecting assembly support rod 26 extends perpendicularly out from vertical frictionless slide 24 and supports a deflecting assembly 28. Deflecting assembly 28 includes a plate support 30 which is pivotably secured to rod 26. A plate holder 32 is supported by plate support 30 and holds a deflecting plate 34. As will be discussed in greater detail hereinbelow, plate 34 defines a deflecting surface 35 for deflecting a portion, such as a wing, of an elastomeric weatherstrip. Again, due to the extremely small coefficient of friction between frictionless slide 24 and mount plate 25, the vertical component of any force applied to the plate 34 is accurately transmitted to the load cell 22.

Base plate 12 also supports a horizontal-vertical positioning assembly 36 for supporting and positioning a weatherstrip with respect to deflecting assembly 28.

The horizontal-vertical positioning assembly 36 includes an adapter 38. A horizontal positioning block 42 is rigidly affixed to a horizontal mounting plate 40, the latter of which is secured to the plate 12. A horizontal positioning device 44, such as a micrometer, is fixed to horizontal positioning block 42. A horizontal slide 46 supports adapter 38 and is capable of linear reciprocation with respect to horizontal mounting plate 40. The travel of slide 46 is guided by horizontal guides 48a and 48b. A traveling end 45 of the horizontal positioning device 44 connects to the horizontal slide 46 so that longitudinal movement of end 45 is transmitted thereto. Accordingly, by rotating the adjustment end 45 of horizontal positioning device 44, such as in the case of its being a micrometer, either clockwise or counterclockwise, horizontal slide 46 is made to move parallel to a longitudinal axis X either away from or toward horizontal positioning block 42. In this manner, the operator is able to control the longitudinal positioning of horizontal-vertical positioning assembly 36.

Secured to a face 37 of adapter 38 is a stationary vertical mounting plate 50 which supports vertically oriented guides 58a and 58b. A vertical slide 56 is coupled to plate 50 via guides 58a and 58b. Guides 58a and 58b are arranged to restrict the movement of slide 56 in the direction of a vertical axis Z. A vertical positioning block 52 is rigidly affixed to vertical slide 56. A vertical positioning device 54, such as a micrometer, is fixed to the vertical positioning block 52. A traveling end 55 of positioning device 54 is connected to plate 50. Accordingly, rotation of the adjustment end 45 of horizontal positioning device 44, in the case of its being a micrometer, results in the vertical positioning block 52, and hence the vertical slide 56, being displaced parallel to vertical axis Z. A weatherstrip supporting structure 60 is coupled to slide 56.

By way of comparison, note that while vertical positioning block 52 is movable with respect to base 12, horizontal positioning block 42 is stationary with respect to the base. Conversely, shaft 53 of the device 54 is axially stationary with respect to the base 12, while shaft 43 of the horizontal positioning device 44 is axially movable with respect to base 12. These features enable horizontal displacement of the vertical-horizontal positioning assembly 36 and vertical displacement of weatherstrip supporting structure 60.

Weatherstrip supporting structure 60 includes a backplate 61 which is secured to vertical slide 56. End supports 62 extend perpendicularly from each end of backplate 61. A weatherstrip holder 64 is supported by end supports 62 to be pivotable about a pivot axis 66. The end supports 62 each define an arcuate slot 70 within which travel thumb screws 68 (only one is shown) which are attached to weatherstrip holder 64. In this manner, the orientation of the weatherstrip holder 64 can be varied about pivot axis 66 and secured in place by thumb screws 68.

In order to assure the precision with which the apparatus 10 is able to measure the force exerted on load cell 22, it is important that the base 12 be horizontally oriented during the measurement process. For this purpose, base 12 is supported by adjustable feet 74, which are independently variable to accommodate for apparatus 10 being placed on an irregular surface. Further toward this purpose, attached to the base are levelling devices 72a and 72b for determining when the base 12 is properly oriented.

Figure 2:
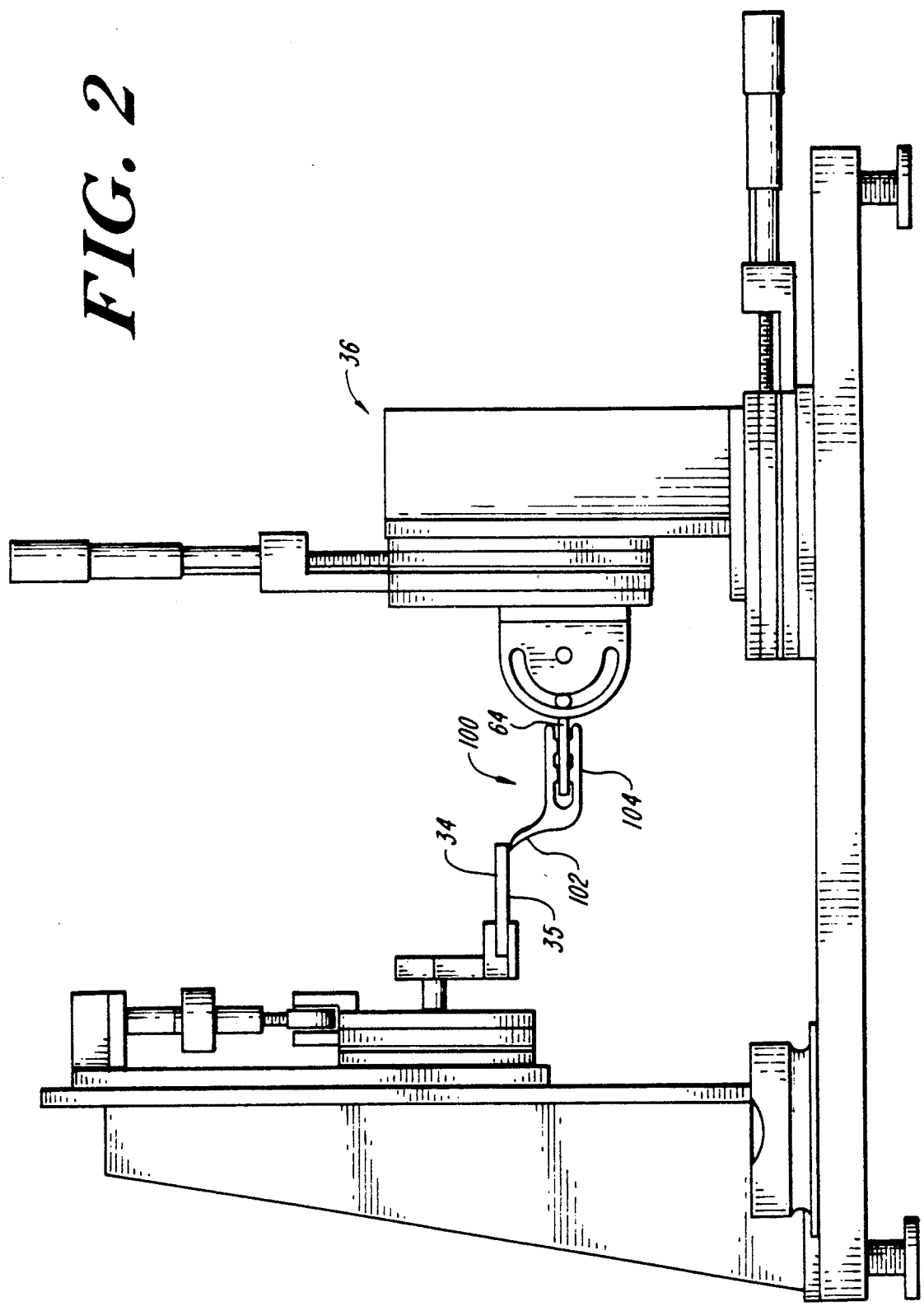
FIG. 2 is a side view of the apparatus shown in FIG. 1.

FIG. 2 is a side view of apparatus 10, wherein a section of an illustrative elastomeric weatherstrip 100 has been mounted on weatherstrip holder 64. It should be understood however, that while a particular configuration is described above, in practice of the present invention, a variety of weatherstrip holders 64 can be constructed for supporting a variety of weatherstrips. The vertical-horizontal positioning assembly 36 is disposed so that a wing 102 of weatherstrip 100 is just barely out of contact with deflecting surface 35 of plate 34. In this position, the wing 102 is in its naturally relaxed position.

Figure 3:
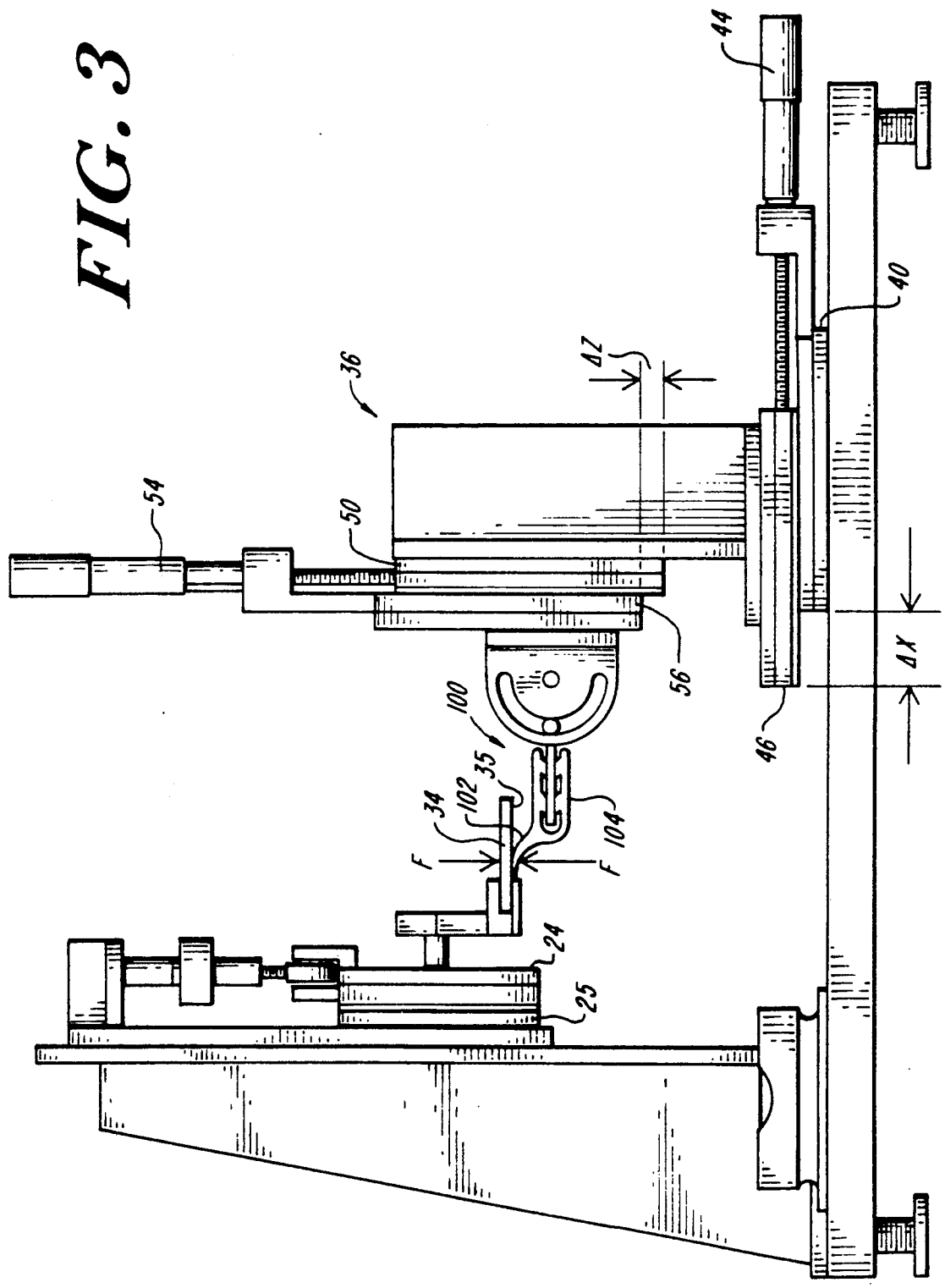
FIG. 3 is a side view of the apparatus shown in FIG. 1 wherein a support structure has been moved into a position suitable for causing a portion of an illustrative weatherstrip to be deflected.

FIG. 3 shows the apparatus in a force measuring mode. That is, vertical-horizontal positioning assembly 36 has been manipulated so as to cause deflecting surface 35 of plate 34 to deflect wing 102 of weatherstrip 100. By appropriately adjusting horizontal positioning device 44, horizontal slide 46 is displaced with respect to horizontal mounting plate 40. This displacement is represented in FIG. 3 as ΔX. Accordingly, this displacement is transmitted to vertical-horizontal positioning assembly 36 which results in weatherstrip 100 being positioned underneath plate 34. Once weatherstrip 100 has been so positioned, the vertical positioning device 54 is adjusted to displace slide 56 vertically with respect to the mounting plate 50. This displacement is shown in the figure as ΔZ. As a result, weatherstrip supporting structure 60 is correspondingly displaced vertically to bring wing 102 of weatherstrip 100 into contact with deflecting surface 35 of plate 34. This will cause wing 102 to be deflected, thereby resulting in a force being exerted on plate 34 by wing 102 the vertical component of which is represented by arrow F.

Vertical component force F is the force that will be detected by load cell 22. Of course, by Newton's Third Law, an equal and opposite component force, say, F', will also be exerted by plate 34 on wing 102. Force F' is a component of the force that actually causes wing 102 to deflect. By implication, therefore, detection of component force F is detection of component force F'.

Figure 4:
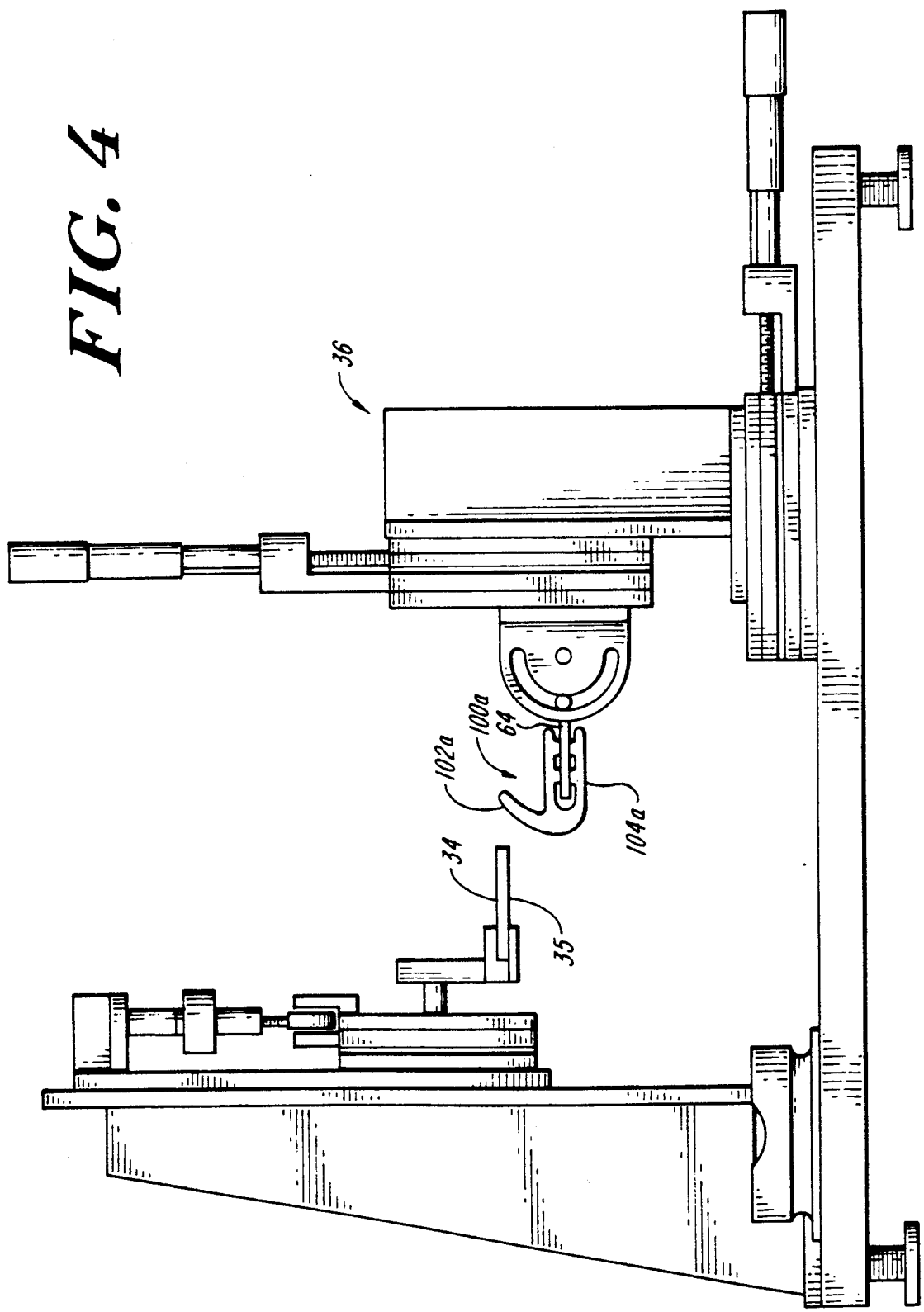
FIG. 4 is a side view of the apparatus shown in FIG. 1 supporting another illustrative weatherstrip just prior to deflection.
Figure 5:
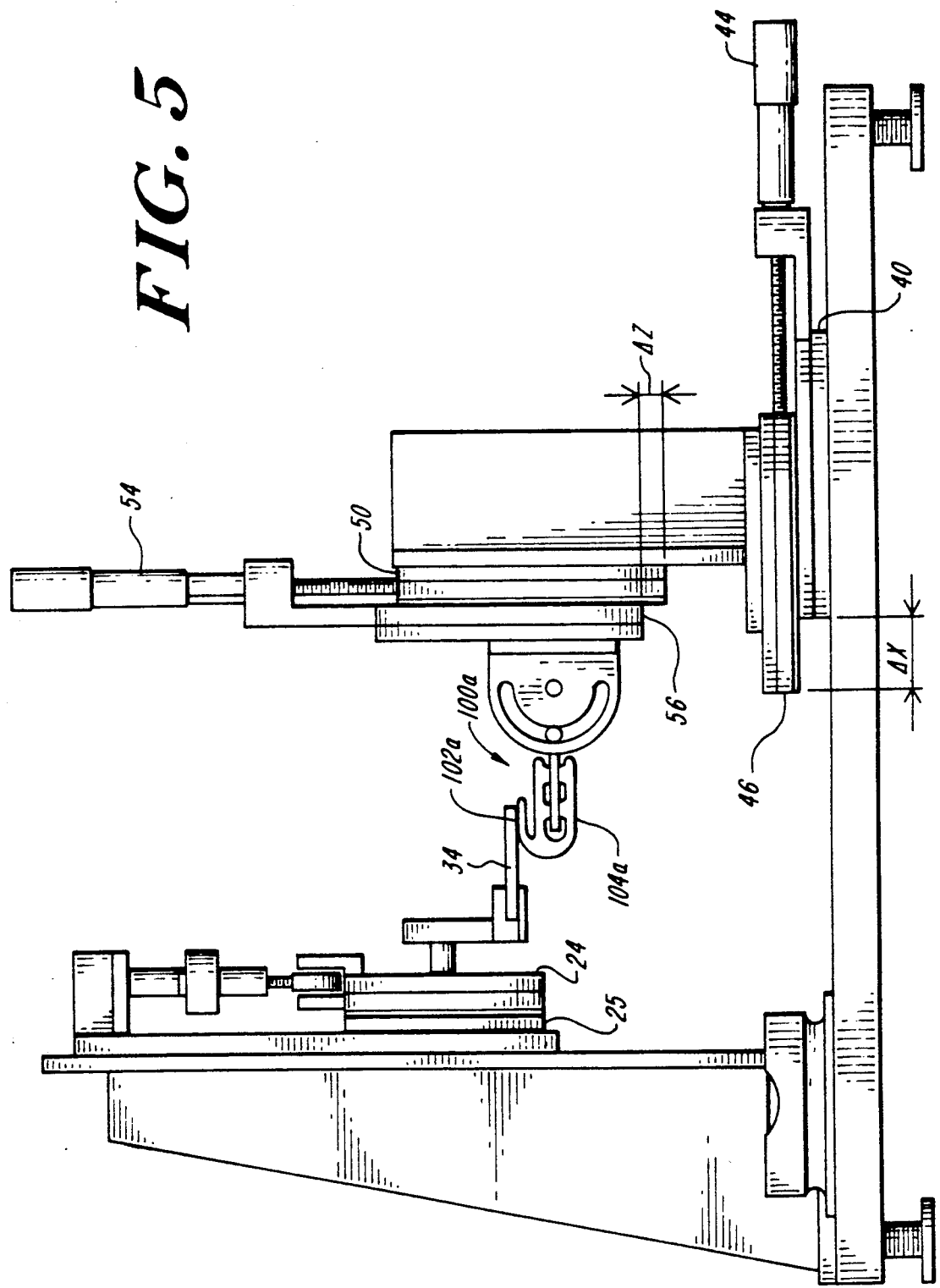
FIG. 5 is a side view of the apparatus and illustrative weatherstrip shown in FIG. 4 during deflection of a portion of the weatherstrip.

FIG. 4 is a side view of apparatus 10, wherein a section of another illustrative elastomeric weatherstrip 100a has been mounted on weatherstrip holder 64. Note that elastomeric weatherstrip 100a includes a rearwardly projecting wind 102a as opposed to the forwardly projecting wing 102 of elastomeric weatherstriP 100. In FIG. 4, the vertical-horizontal positioning assembly 36 is disposed so that wing 102a of weatherstrip 100a is out of contact with deflecting surface 35 of plate 34 but extends above plate 34. From this position, by appropriately adjusting horizontal positioning device 44, horizontal slide 46 is displaced with respect to horizontal mounting plate 40 by distance ΔX. This displacement is transmitted to vertical-horizontal positioning assembly 36 which results in wing 102a being deflected, as shown in FIG. 5, by deflecting surface 35 of plate 34. This will result in wing 102a exerting a force on plate 34 which has a substantial horizontal component.

Figure 6:
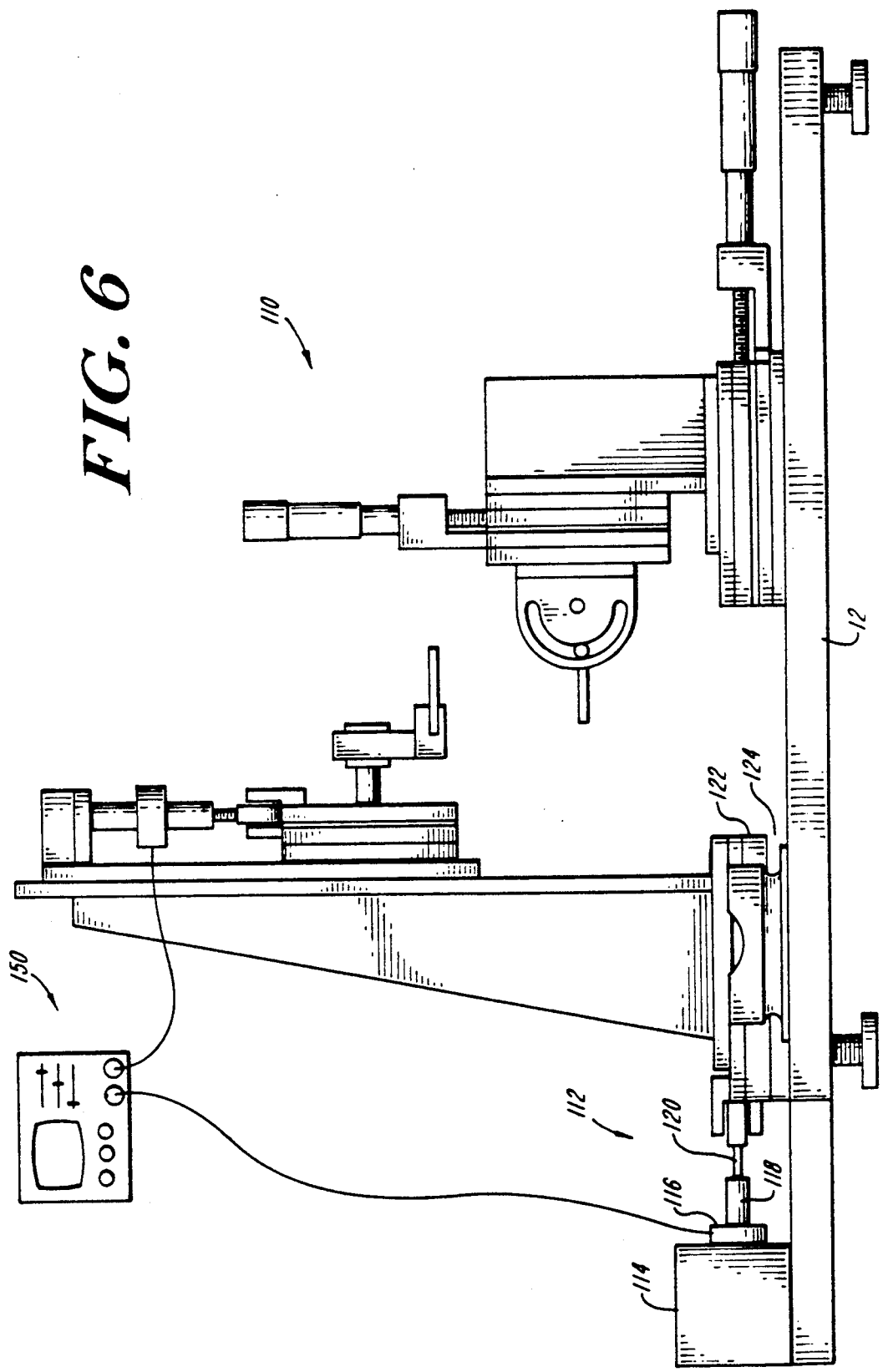
FIG. 6 is a side view of another embodiment of an apparatus constructed in accordance with the present invention.
Figure 7A:
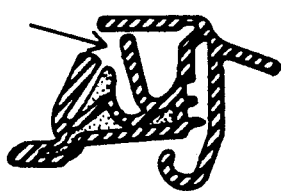
FIGS. 7a through 7f are cross-sectional views of an illustrated array of weatherstrip profiles which the apparatuses of FIGS. 1 and 6 are well suited for testing, the arrows indicating the portion of the weatherstrip profiles being tested.
Figure 7B:
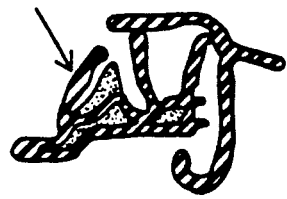
Figure 7C:
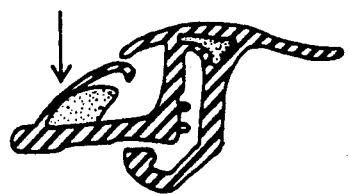
Figure 7D:
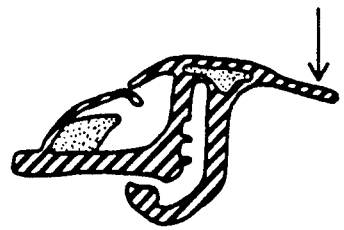
Figure 7E:
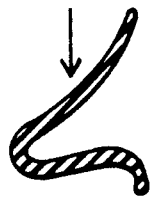
Figure 7F:
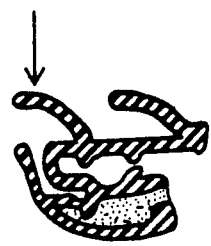
Figure 8A:
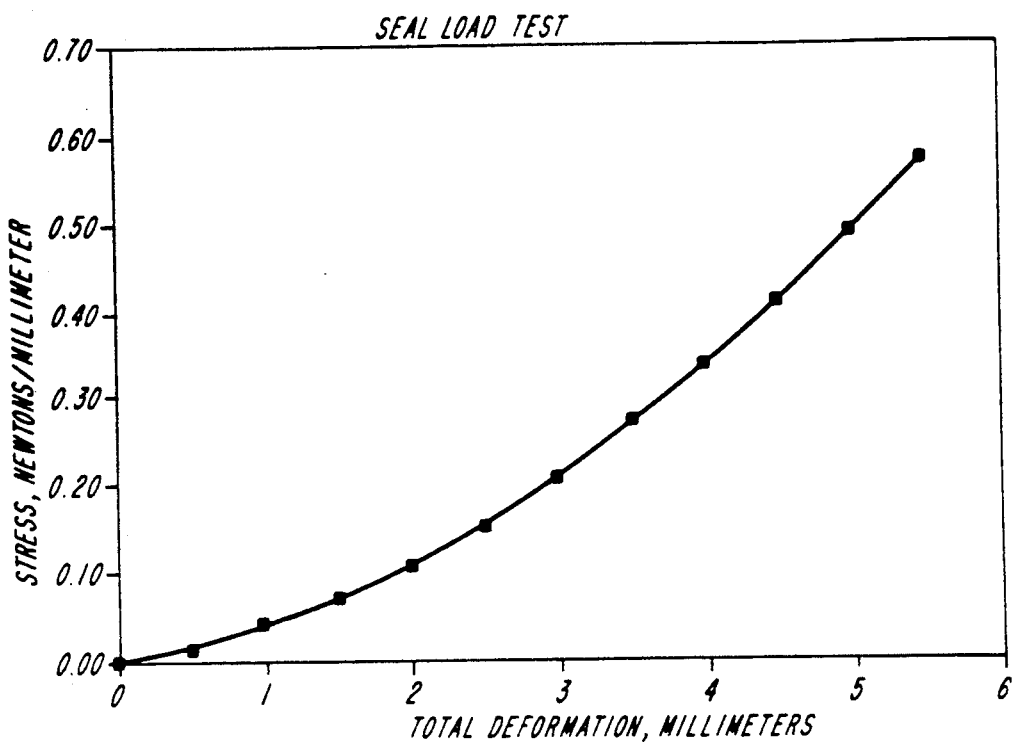
FIGS. 8a through 8f are graphs representing the relationship between seal load and total deflection, the graphs corresponding to the test portions and weatherstrip profiles depicted in FIGS. 7a through 7f, respectively.
Figure 8B:
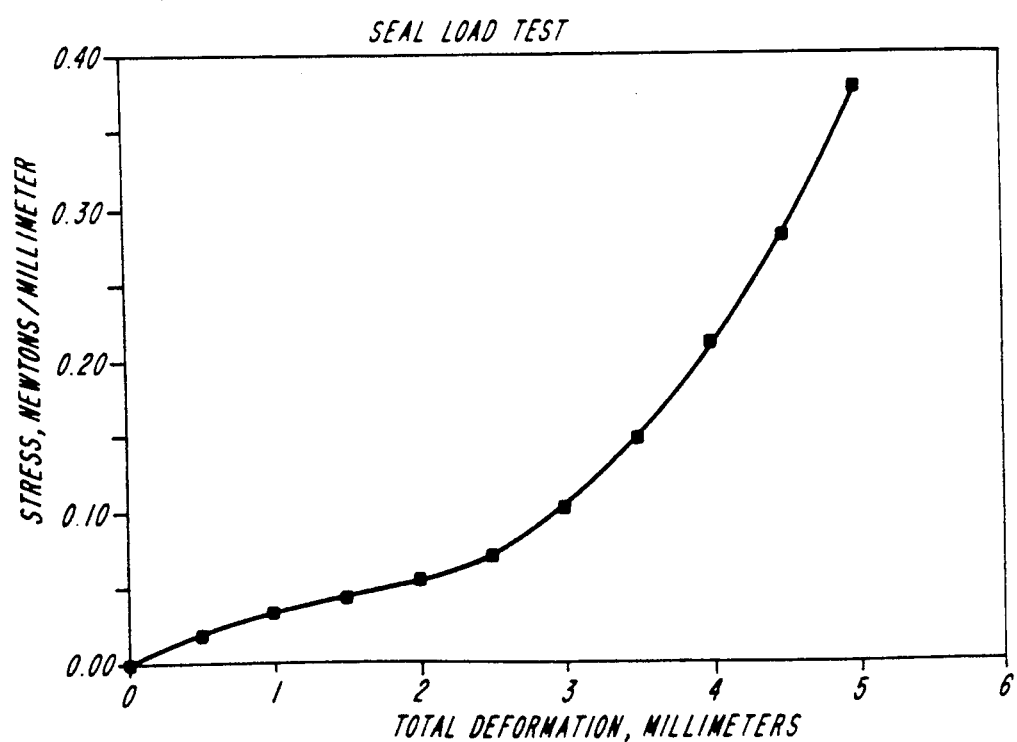
Figure 8C:
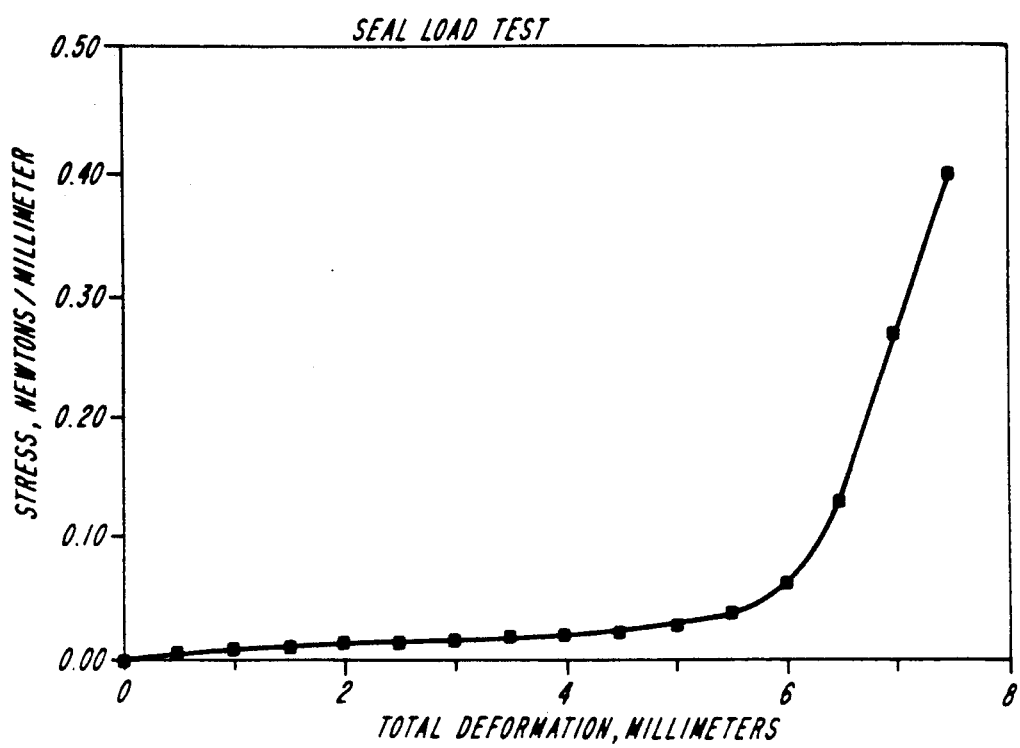
Figure 8D:
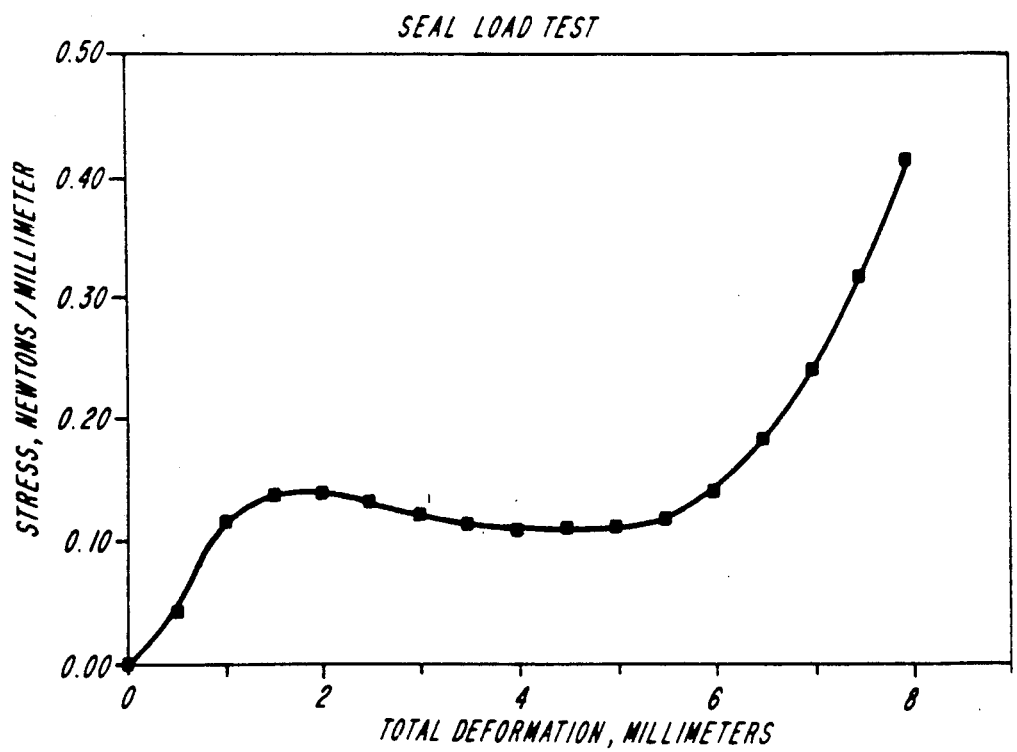
Figure 8E:
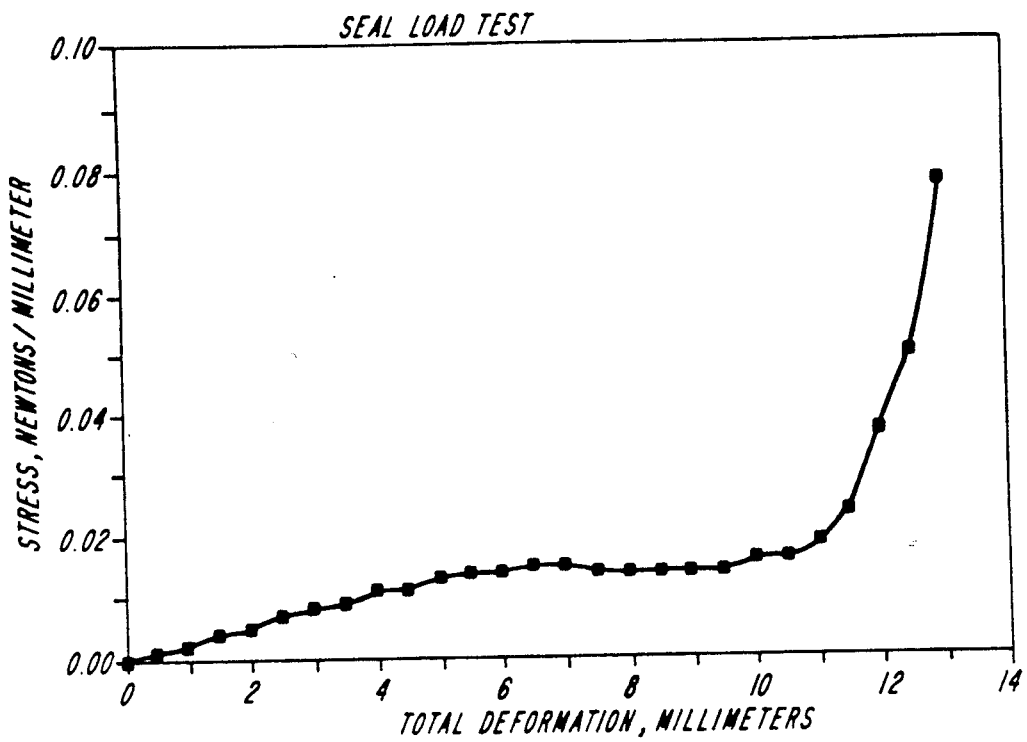
Figure 8F:
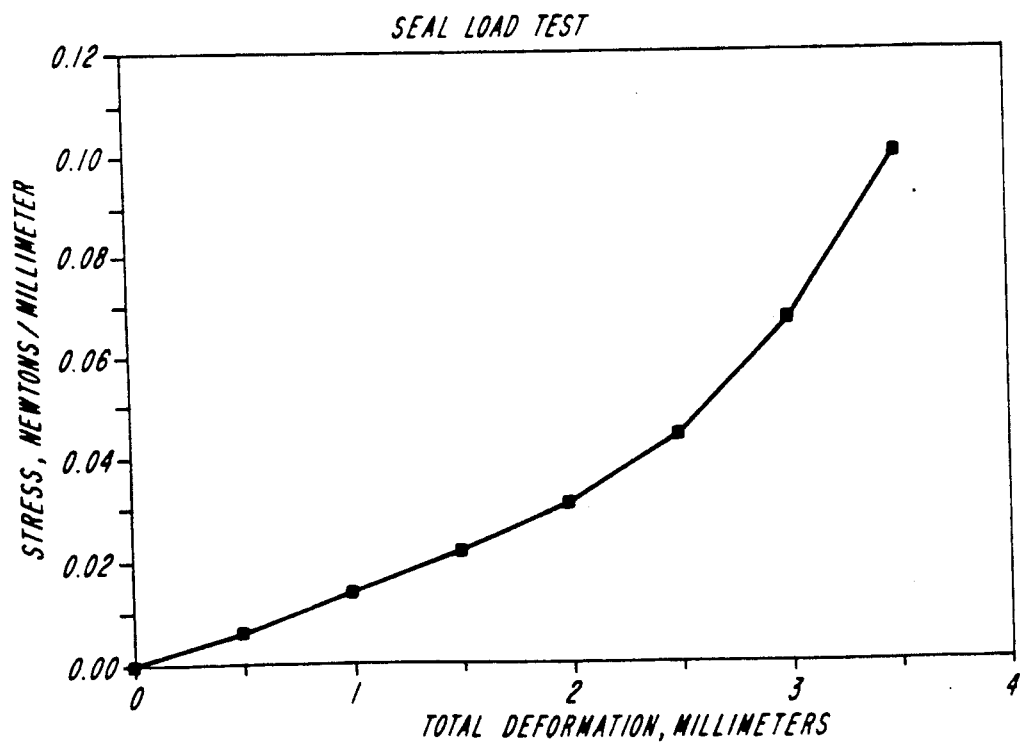
Figure 9A:
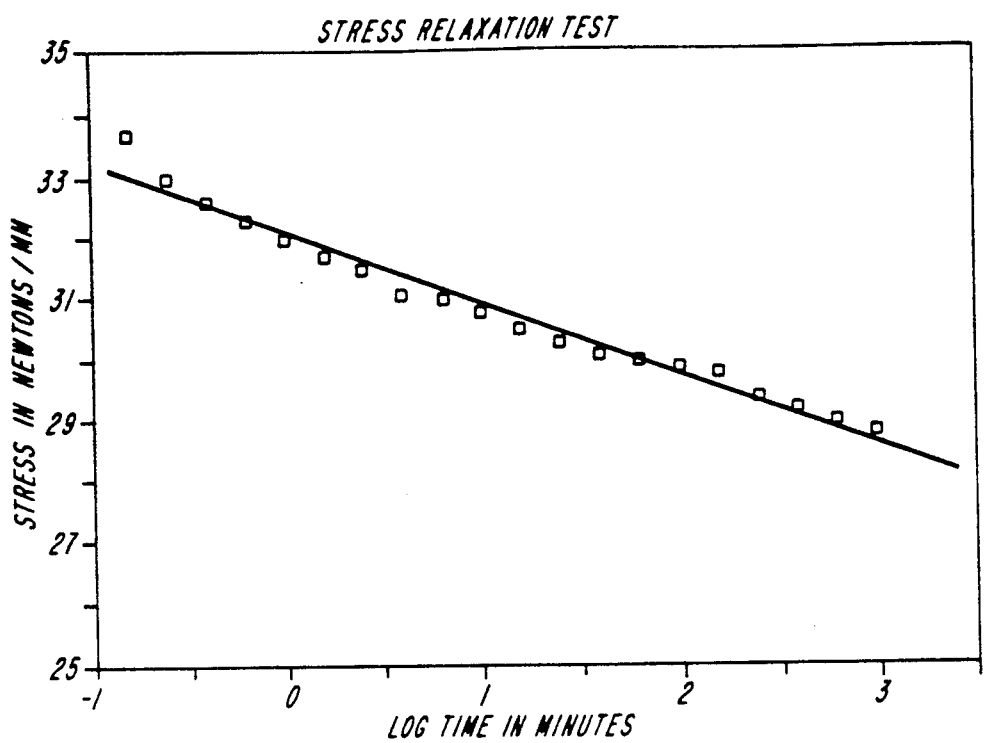
FIGS. 9a through 9f are graphs representing the stress relaxation rate of the test portions and weatherstrip profiles depicted in FIGS. 7a through 7f, respectively.
Figure 9B:
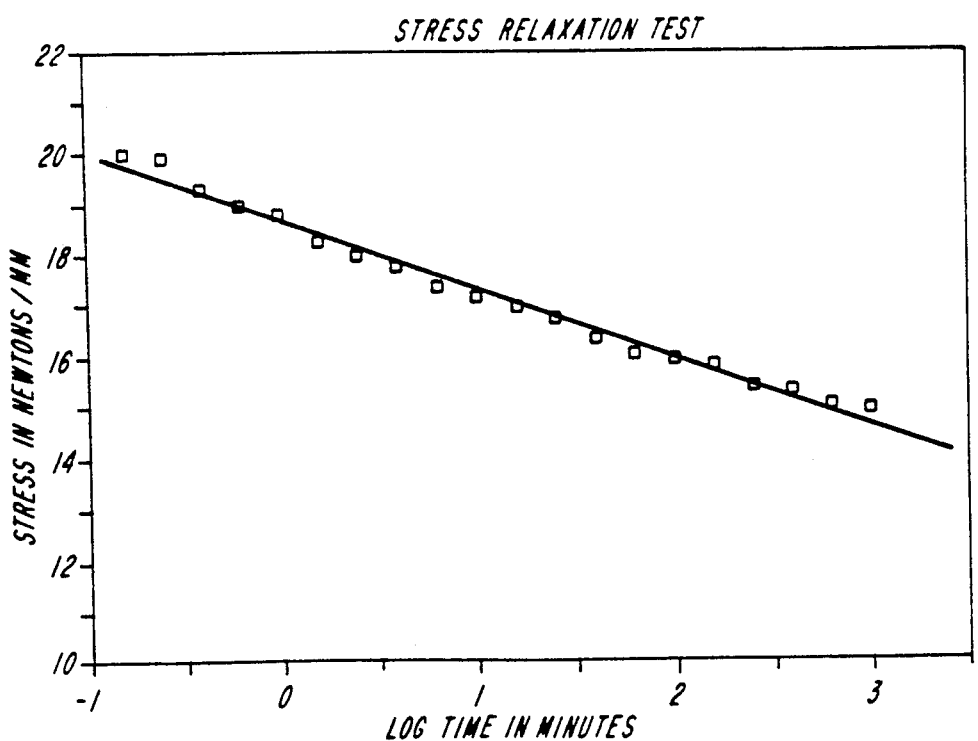
Figure 9C:
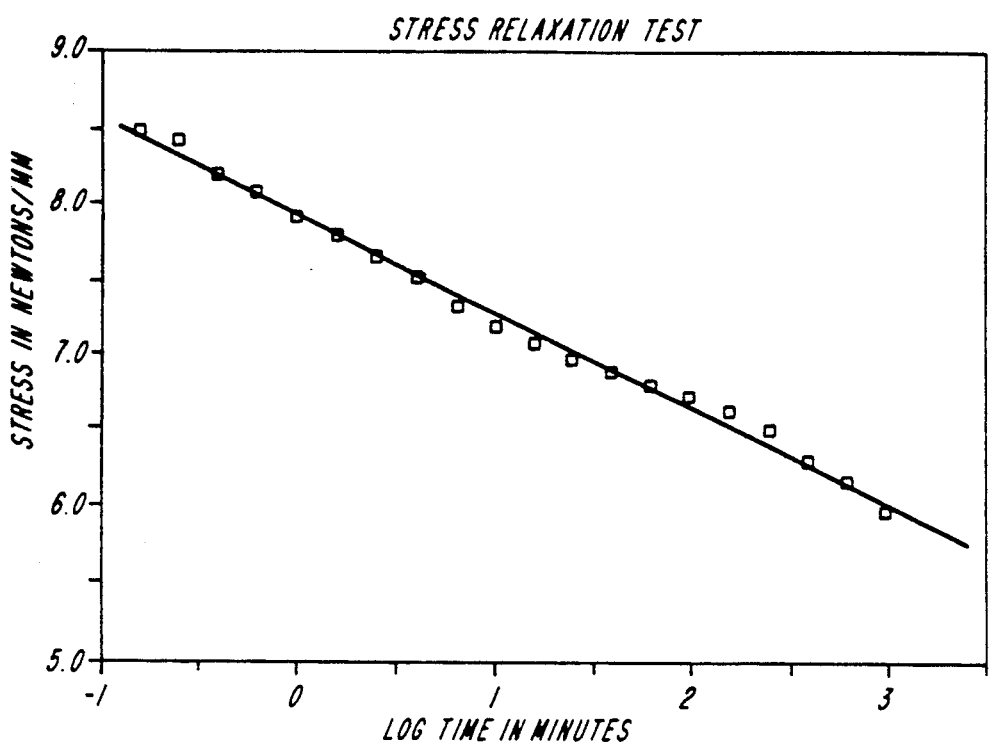
Figure 9D:
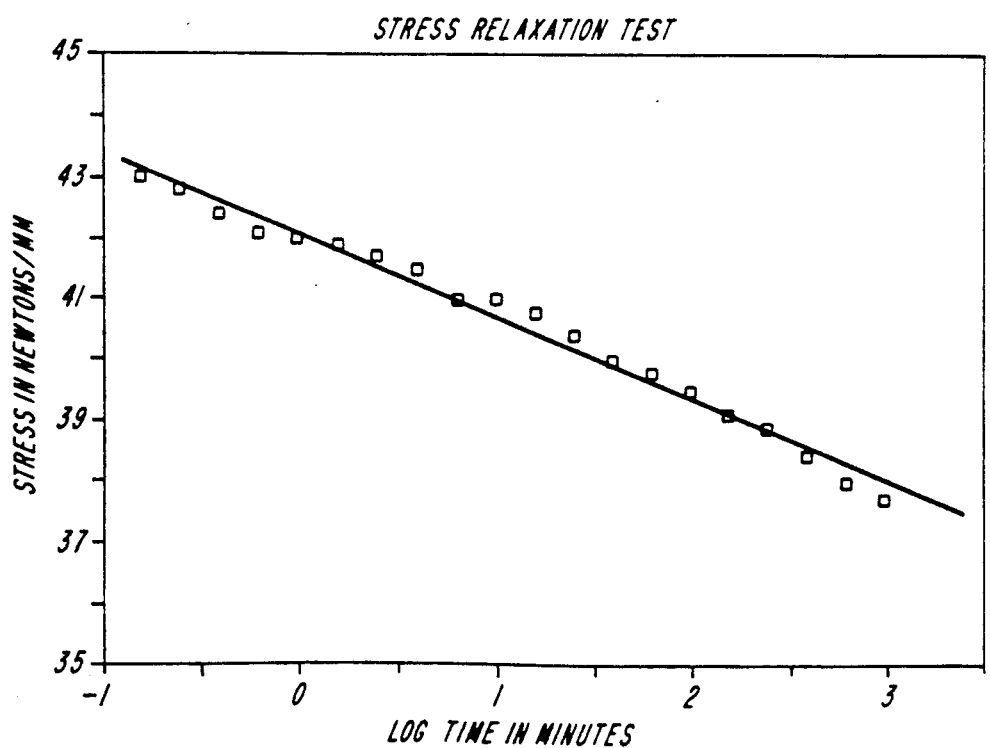
Figure 9E:
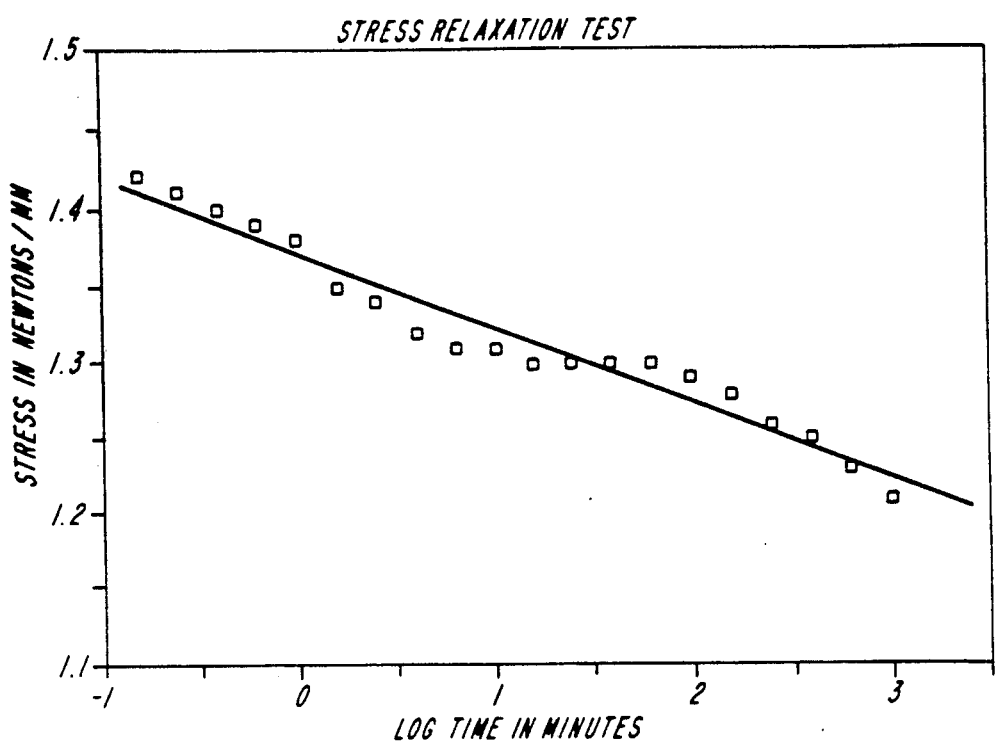
Figure 9F:
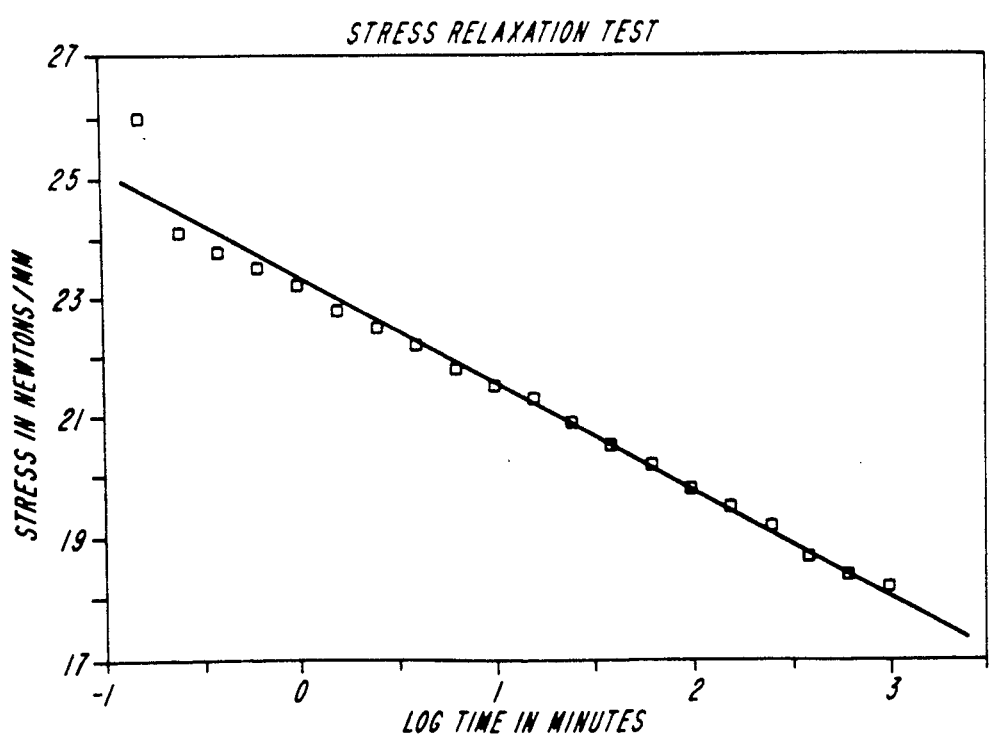
Figure 10A:
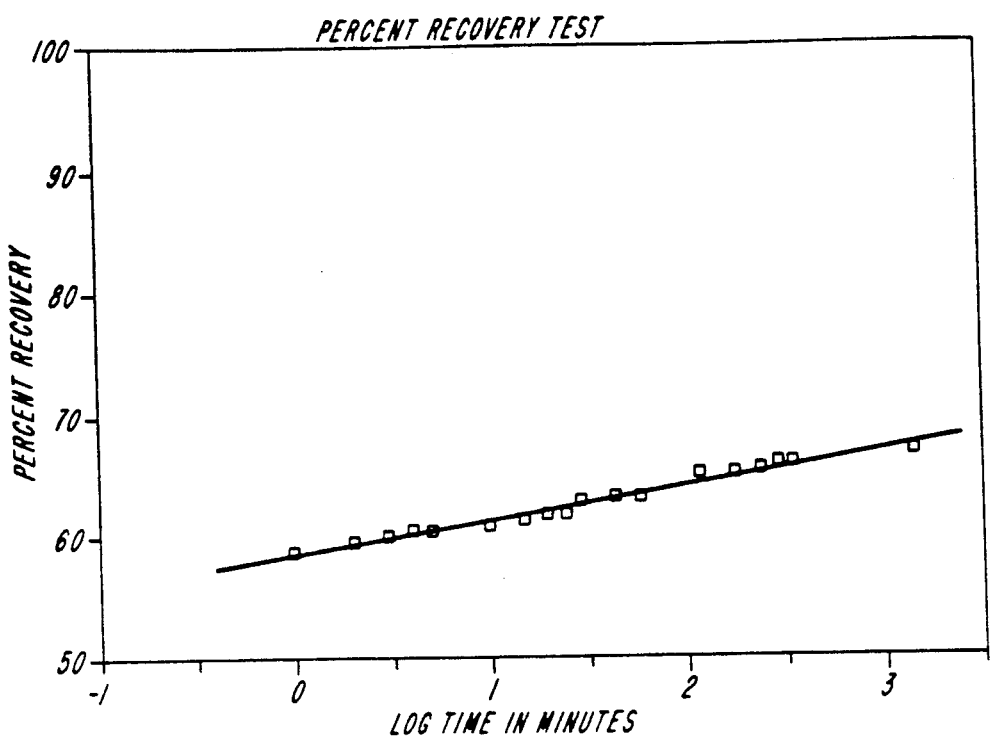
FIGS. 10a through 10f are graphs representing the seal recovery rate of the test portions and weatherstrip profiles depicted in FIGS. 7a through 7f, respectively.
Figure 10B:
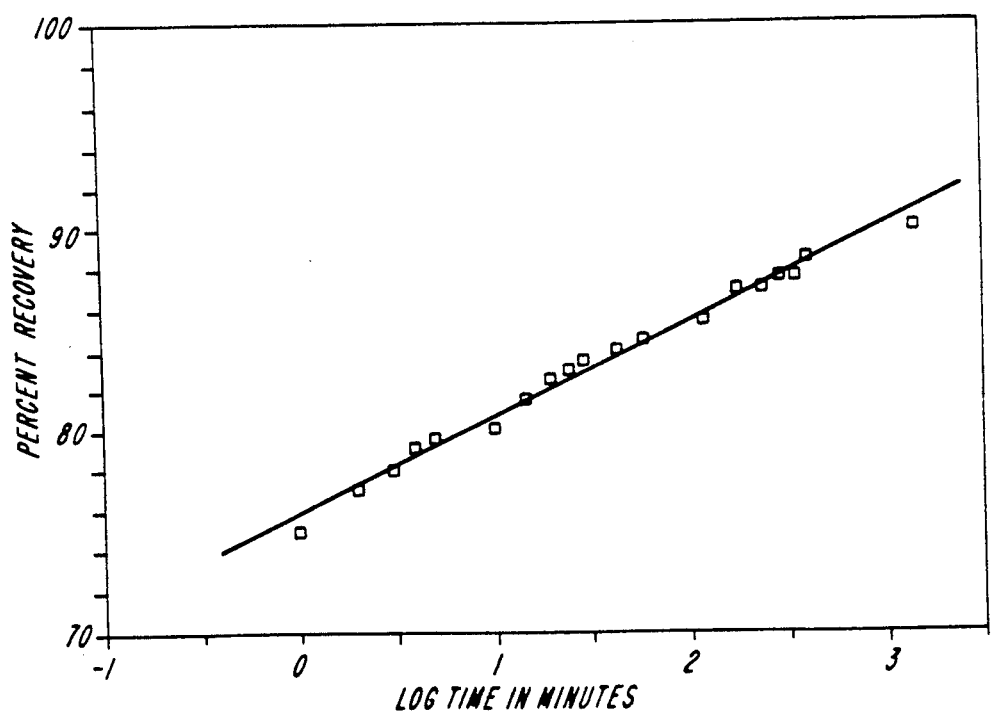
Figure 10C:
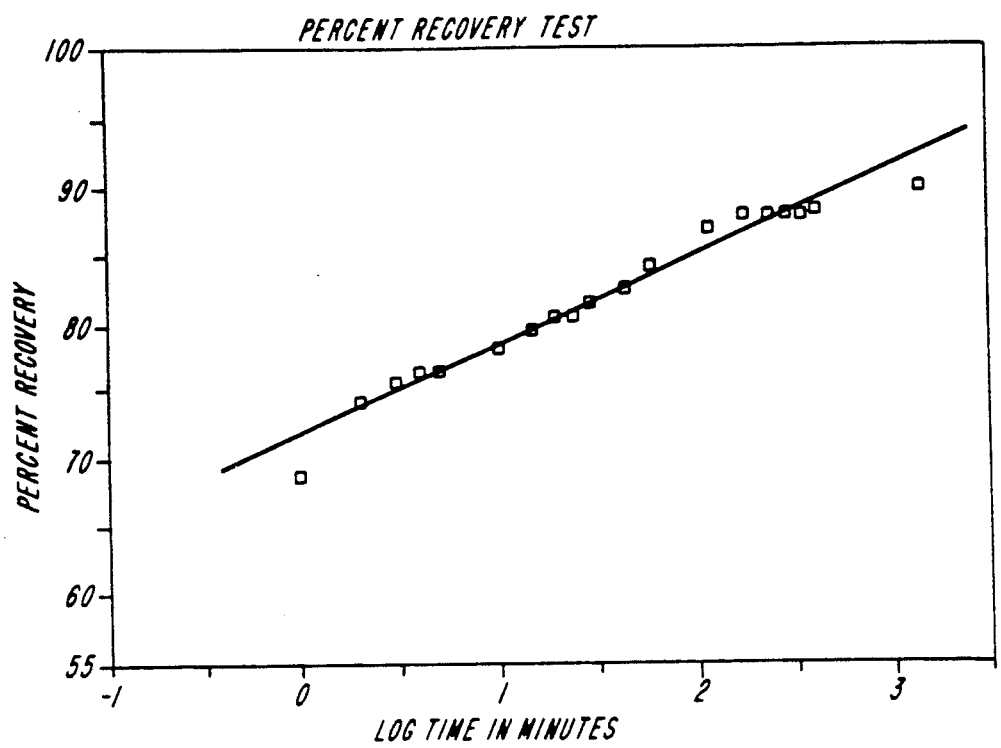
Figure 10D:
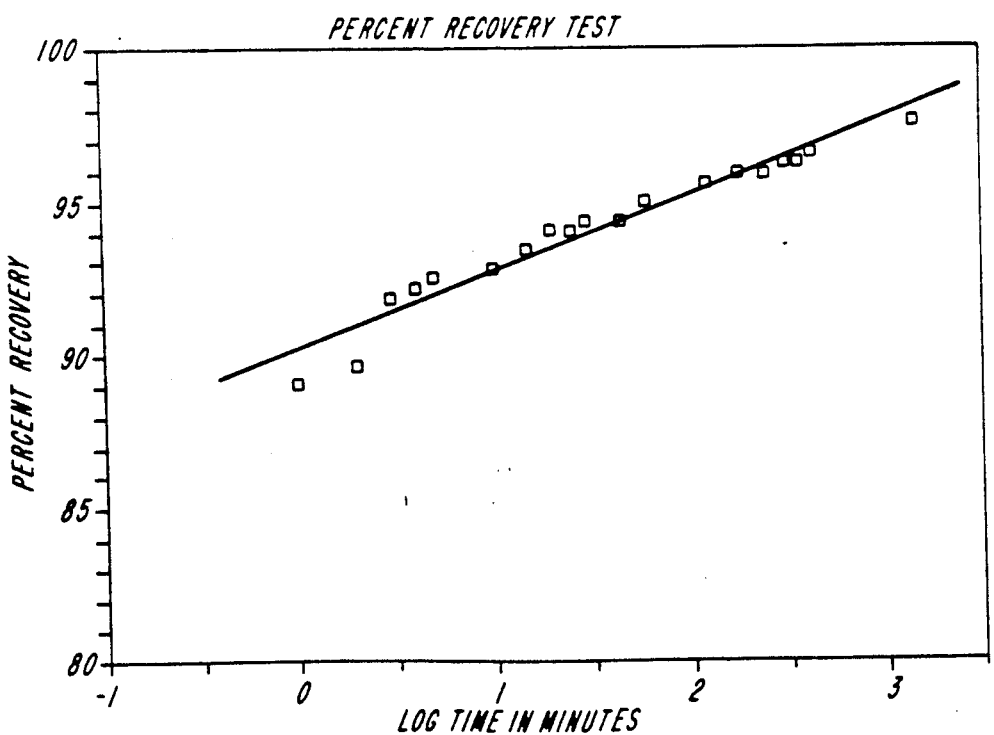
Figure 10E:
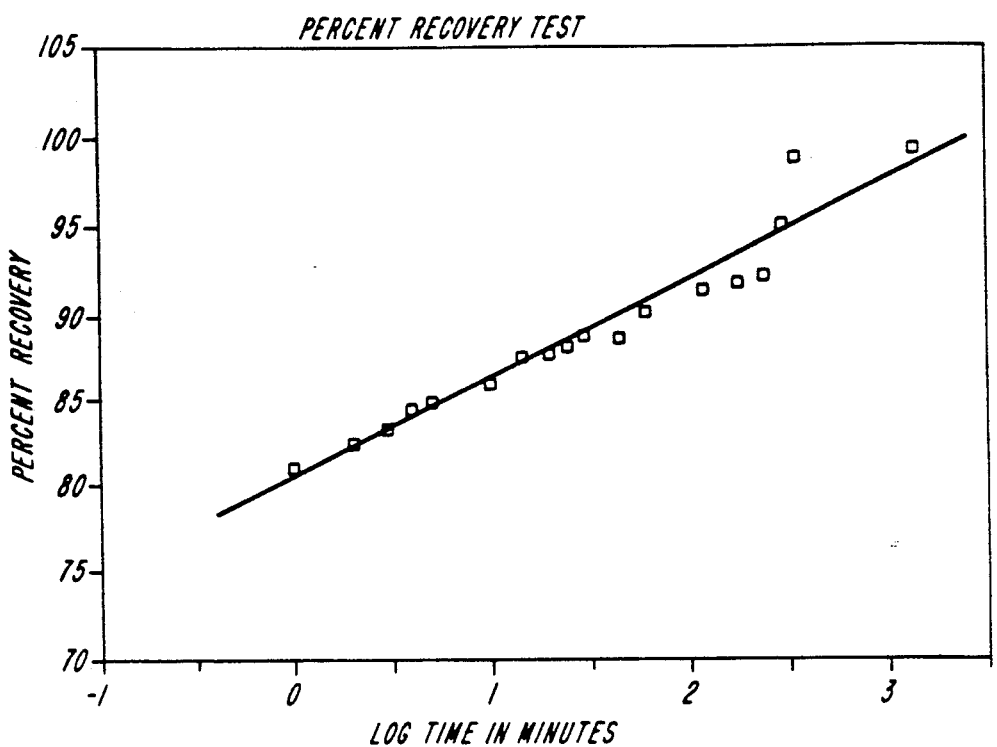
Figure 10F:
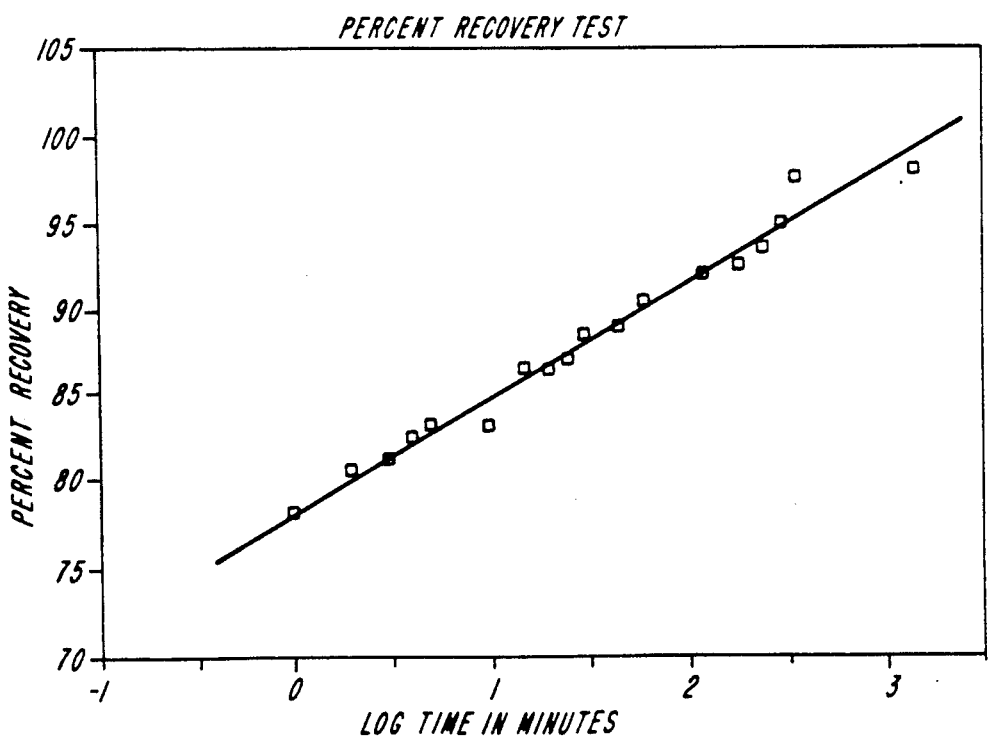

For measuring the total force exerted on plate 34 by deflection of the type depicted in FIG. 5, an embodiment of the invention shown in FIG. 6 is particularly well suited. In this embodiment, an apparatus 110 includes, in addition to the features of apparatus 10, a horizontal force measuring assembly 112 and a processor 150 for continually monitoring the force components measured by the force measuring assemblies 11 and 112. The horizontal force measuring assembly 112 includes a horizontal load cell bracket 114 which is rigidly secured to base 12. A load cell 116 is mounted on horizontal load cell bracket 114. A horizontal load cell mount 118 connects load cell 116 to a coupling 120 which is secured to a horizontal frictionless slide 122 which frictionlessly reciprocates via an intermediate mounting plate 124 along axis X. Intermediate mounting plate 124 is rigidly secured to base 12. By this arrangement, the horizontal component of a force exerted by a deflected wing or bulb of a weatherstrip on plate 34 will be transmitted to load cell 116, in conjunction with the load cell 22. Therefore, the total force exerted by a deflected weatherstrip on plate 34 can be broken down into its vertical and horizontal components by operation of load cells 22 and 116, respectively.

Processor 150 continuously monitors the force measured by load cells 22 and 116 and is able to provide data representative of a wide variety of phenomena. For example, processor 150 is able to process information received from the load cells 22 and 116 to determine such properties as average horizontal force component, average vertical force component, maximum and minimum horizontal and vertical force components, and various time related properties of the force components. For the purpose of carrying out the tests described herein below, this information is extremely important. While many commercially available processors have been found to be suitable for this purpose, the OMEGA model OM900, as programmed in an ordinary fashion for carrying out the above-described mathematical operations, has been found to be well suited for the present application. For simply displaying the values measured by load cells 22 and 116, an OMEGA model DP350 is well suited. If desired, the display unit can be arranged to provide data to a chart recorder such as an OMEGA model RD1202. Of course, other commercially available units will perform equally as well.

Shown in FIGS. 7a through 7f are typical weatherstrip profiles that can be tested using the apparatus of the present invention. The arrows in each figure indicates the portion of the particular profile which can be subjected to the following described tests. The weatherstrip 100 depicted in FIGS. 2 and 3 is shown having a simple profile for ease of illustration only. It should be understood, however, that the discussion herein pertaining to the behavior and properties of wing 102 is equally applicable to the weatherstrip profiles shown in FIGS. 7a through 7f.

It is an important characteristic of the apparatuses 10 and 110 that the force exerted by the deflecting surface 35 be evenly distributed along the length of the wing of the weatherstrip being tested. It is for this purpose that the deflecting assembly 28 is rotatable about the support rod 26. As a result, when the vertical—horizontal positioning assembly 36 is manipulated to bring the wing 102 of the weatherstrip 100 into contact with the deflecting surface 35 of the plate 34, the deflecting assembly 28 will pivot about the support rod 26 to ensure that the deflecting surface 35 is parallel to the portion of the weatherstrip being deflected. It should be understood that while the deflecting plate 34 will typically define the deflecting surface 35 to be planar, depending on the specific application and the geometry of the wing or bulb being tested, this feature of the invention can be varied so long as the force exerted by the deflecting surface 35 on the weatherstrip is evenly distributed. Also, for the purpose of testing particular portions of certain weatherstrip profiles, such as, for example, that depicted in FIG. 7a, it may be necessary to remove sections of the weatherstrip to provide access to the wing or bulb to be tested.

To determine the amount of force, i.e., seal load, required to deform a wing or bulb of a weatherstrip, the following steps are taken. A section of weatherstrip such as that shown in FIGS. 7a through 7f is mounted on a suitable weatherstrip holder 64 which is then properly mounted between end supports 62 of weatherstrip supporting structure 60. The weatherstrip holder 64 is then properly adjusted by adjusting thumb screws 68 in the arcuate slots 70 to ensure that the wing or bulb to be tested is as nearly as possible parallel to deflecting surface 35 of plate 34. The horizontal positioning device 44 is adjusted so that the section of the weatherstrip is positioned directly under deflecting plate 35 and then vertical positioner 54 is adjusted until wing 102 just barely contacts deflecting surface 35. This can be verified by monitoring the reading delivered by load cell 22 which will change as soon as wing 102 contacts deflecting surface 35. At this point, a reading is taken from the vertical positioning device 54 to determine the undeflected position of wing 102 of weatherstrip 100.

Once the undeflected position of wing 102 has been determined, vertical positioning device 54 is adjusted to result in the wing or bulb being deflected a specified distance. For example, the vertical positioning device 54 can be systematically adjusted so that the wing or bulb is deflected 0.020 inches every 15 seconds until maximum deformation occurs. Maximum deformation occurs when, due to compression of weatherstrip 100, vertical positioning device 54 can no longer be rotated in the clockwise direction. When maximum deformation occurs, a reading is taken from the vertical positioning device 54 and the test s discontinued.

It has been found that while load cell readings can be manually recorded for each adjustment of the vertical positioning device 54, it is particularly beneficial if processor 150 is arranged to supply a chart recorder with this information. By running the chart recorder at, for example, a speed of 2 centimeters per minute to 6 centimeters per minute, a chart is generated which neatly indicates the force required to deflect wing 102 each incremental distance.

For purposes of illustration, FIGS. 8a through 8f are graphic representations of the relationship between force exerted by a deflected portion of a weatherstrip profile and the distance of the total deflection based on data collected in accordance with tests performed on the weatherstrip profiles depicted in FIGS. 7a through 7f, respectively. By generating such graphs for weatherstrips which are known to provide effective sealing, a specification can be determined to which manufactured weatherstrips should comply. By deflecting a portion of a weatherstrip and monitoring the rate at which the force exerted by the deflected portion decreases, apparatus 110 can be used to determine stress relaxation. For this purpose, the portion of the weatherstrip will typically be deflected to either maximum deformation, as determined in the manner set forth above, or to the extent to which it will be deflected when in use. As with the above described seal load test, it may be desirable to arrange processor 150 to provide information to a chart recorder running at a speed of, for example, 10 centimeters per hour. This will result in a chart being generated which is representative of the stress relaxation rate of a given portion of a selected weatherstrip. Typically, a stress relaxation test will be run for periods of from a few to 350, 1000, or 4000 minutes. Of course this period can be varied to serve individual goals.

FIGS. 9a through 9f are graphic representations of stress relaxation for the indicated portions of the elastomeric weatherstrip profiles depicted in FIGS. 7a through 7f respectively. The graphs clearly indicate that the force exerted by a deflected wing or bulb of a weatherstrip is linearly and inversely proportional to the logarithm of the time period of deflection. This stands for the proposition that as time passes, a deflected wing or bulb of an elastomeric weatherstrip relaxes. That is, the deflected wing or bulb exerts a smaller force.

A third characteristic of an elastomeric weatherstrip that affects the weatherstrip's ability to provide effective sealing between the edge of an opening in a motor vehicle body and a closure element for that opening is the weatherstrip's recovery rate. "Seal recovery rate" is the rate at which a deflected portion of an elastomeric weatherstrip returns to its original position after the deflecting force has been removed. The apparatuses 10 and 110 can be used to measure seal recovery rate in the following way.

A section of an elastomeric weatherstrip, such as, for example, weatherstrip 100, is affixed to the weatherstrip holder 64 and positioned by the horizontal positioning device 44 to be underneath deflecting plate 34. The vertical positioning device 54 is then adjusted so that wing 102 just barely contacts the deflecting surface 35 of deflecting plate 34. This can be verified, as discussed above, by monitoring the response of load cell 22. Once weatherstrip 100 has been positioned in this manner, a reading is recorded from the vertical positioning device 54 to mark the undeflected position of wing 102. The vertical positioning device 54 is then adjusted to raise weatherstrip 100 and cause deflecting surface 35 of plate 34 to deflect wing 102 to a selected deformation.

To determine seal recovery rate, wing 102 is deflected for a predetermined period of time. Experience has shown that utilizing a deflection period of 30 minutes produces meaningful data. Of course, for various purposes other deflection periods may be more well suited. After this period, the vertical positioning device 54 is rotated so that wing 102 is brought out of contact with deflecting surface 35 and immediately brought slightly back into contact with deflecting surface 35, as determined by a reading change delivered by load cell 22, so that the new position of wing 102 can be recorded based on the reading of vertical positioning device 54. The vertical positioning device 54 is then adjusted to lower weatherstrip 100 to provide sufficient clearance between wing 102 and deflecting plate 34 so that wing 102 is allowed to recover at its natural rate. The wing's position is then determined at set intervals of time by adjusting the vertical positioning device 54, monitoring the readings given by load cell 22 to determine when wing 102 is in contact with deflecting surface 35, and recording the reading given by vertical positioning device 54 at these points.

FIGS. 10a through 10f are graphs of data obtained in accordance with the above-described method for determining seal recovery. The graphs correspond to seal recovery tests performed on the indicated portions of the various weatherstrip profiles depicted in FIGS. 7a through 7f, respectively. It is clear from the graphs that the relationship between the percent recovery of a deflected portion of a weatherstrip and the logarithm of elapsed time is directly linear.

In order to manufacture weatherstrips that provide effective sealing, it is important that the relationships depicted in FIGS. 8a-8f, 9a-9f, and 10a-10f be maintained as closely as possible. This can be achieved by systematically testing sample weatherstrips during manufacturing runs, and implementing statistical process controls, so that aberrations in weatherstrip quality are quickly discovered and can be addressed. By providing a fast and simple way to monitor seal load, stress relaxation, and percent recovery, therefore, the present invention enables weatherstrips to be manufactured the quality of which is closely controlled. The present invention provides a simple, effective, and economic way for performing such tests so that ultimately, a manufacturer utilizing the present invention can produce superior weatherstrips.

It should be understood that the above described embodiments are merely illustrative of the present invention and that various alterations and additional applications will be readily apparent to those skilled in the art. The invention is to be defined, therefore, not by the preceding description but by the claims that follow.

What is claimed is:

1. An apparatus for measuring quantities related to the force required to deflect along a deflection axis a portion of a resilient weatherstrip, the apparatus comprising
  a member defining a deflection surface which is rotatable about a pivot axis perpendicular to said deflection axis,
  support means for receiving and positioning a strip of weatherstrip with respect to said surface such that a strip received by the support means can be oriented to extend along a longitudinal axis perpendicular to the deflection axis and to the pivot axis with an edge of the received strip running generally parallel to said longitudinal axis and to said surface,
  means for adjusting said support means such that said deflection surface and said edge of said received strip are in contact substantially uniformly along said longitudinal axis to an extent sufficient to cause selected deflection of a portion of said received strip substantially uniformly along said edge, and
  means for measuring the force exerted upon said deflection surface by said received strip portion during said selected deflection.

2. An apparatus as set forth in claim 1 wherein said means for measuring the force exerted on the surface is a vertically mounted load cell arranged in communication with said member for detecting a vertical force component of the force.

3. An apparatus as set forth in claim 1 wherein said means for adjusting said support means includes means for indicating the displacement of said support means due to adjustment.

4. An apparatus as set forth in claim 3 wherein said means for indicating the displacement of said support means includes means for indicating a horizontal component of the displacement and means for indicating a vertical component of the displacement.

5. An apparatus as set forth in claim 1 further comprising
  means for continually monitoring the measured force to determine the rate at which said received strip portion relaxes over a period of time.

6. An apparatus for measuring the relaxation rate of the force required to deflect along a deflection axis a portion of a resilient weatherstrip, the apparatus comprising a member defining a deflection surface which is rotatable about a pivot axis perpendicular to said deflection axis, support means for receiving and positioning a strip of weatherstrip with respect to said surface such that a strip received by the support means can be oriented to extend along a longitudinal axis perpendicular to the deflection axis and to the pivot axis with an edge of the received strip running generally parallel to said longitudinal axis and to said surface, means for adjusting said support means such that said deflection surface and said edge of said received strip are in contact substantially uniformly along said longitudinal axis to an extent sufficient to cause selected deflection of a portion of said received strip substantially uniformly along said edge, means for measuring the force exerted upon said deflection surface by said received strip portion during said selected deflection, and means for continually monitoring the measured force to determine the rate at which said received strip portion relaxes over a period of time.

7. An apparatus as set forth in claim 6 wherein said means for detecting the force exerted on the surface is a vertically mounted load cell arranged in communication with said member for detecting a vertical component of the force.

8. An apparatus as set forth in claim 6 wherein said means for adjusting said support means includes means for indicating the displacement of said support means due to adjustment.

9. An apparatus as set forth in claim 8 wherein said means for indicating the displacement of said support means includes means for indicating a horizontal component of the displacement and means for indicating a vertical component of the displacement.

10. A method for measuring quantities related to the force required to deflect along a deflection axis a portion of a resilient weatherstrip, the method comprising the steps of orienting a strip of weatherstrip to extend along a longitudinal axis perpendicular to the deflection axis with an edge of the strip running generally parallel to said longitudinal axis and to a deflection surface which is rotatable about a pivot axis perpendicular to the deflection axis and to the longitudinal axis, exerting a force on the portion with said deflection surface to cause selected deflection of the portion substantially uniformly along said edge, and measuring the force exerted upon said deflection surface by said strip portion during said selected deflection.

11. A method as set forth in claim 10 further comprising the step of monitoring continually the measured force to determine the rate at which the force exerted by said portion relaxes over a period of time.

12. A method as set forth in claim 10 wherein the step of exerting a force on the portion includes the sub-steps of mounting the weatherstrip on a support, adjusting the support after said orienting step to bring the edge into contact with the deflection surface to an extent sufficient to cause said selected deflection.

13. A method for measuring quantities related to the force required to deflect along a deflection axis a portion of a resilient weatherstrip, the method comprising the steps of orienting a strip of weatherstrip to extend along a longitudinal axis perpendicular to the deflection axis with an edge of the strip running generally parallel to said longitudinal axis and to a deflection surface, mounting the weatherstrip on a support, adjusting the support after said orienting step to bring the edge into contact with the deflection surface to an extent sufficient to cause selected deflection, measuring a horizontal component of the exerted force, and measuring a vertical component of the exerted force.

14. A method for measuring the relaxation rate of a portion of a resilient weatherstrip deflected along a deflection axis, the method comprising the steps of orienting a strip of weatherstrip to extend along a longitudinal axis perpendicular to the deflection axis with an edge of the strip running generally parallel to said longitudinal axis and to a deflection surface which is rotatable about an axis perpendicular to the deflection axis and to the longitudinal axis, exerting a force on the portion with said deflection surface to cause selected deflection of the portion substantially uniformly along said edge, measuring the force exerted upon said deflection surface by said strip portion during said selected deflection, and monitoring continually the measured force to determine the rate at which the portion relaxes over a period of time.

15. A method as set forth in claim 14 wherein the step of exerting a force on the portion includes the sub-steps of mounting the weatherstrip on a support, and adjusting the support after said orienting step to bring the edge into contact with the surface to an extent sufficient to cause said selected deflection.

16. A method for measuring the relaxation rate of a portion of a resilient weatherstrip deflected along a deflection axis, the method comprising the steps of orienting a strip of weatherstrip to extend along a longitudinal axis perpendicular to the deflection axis with an edge of the strip running generally parallel to said longitudinal axis and to a deflection surface, mounting the weatherstrip on a support, adjusting the support after said orienting step to bring the edge into contact with the surface to an extent sufficient to cause said selected deflection, measuring an horizontal component of the exerted force, measuring a vertical component of the exerted force, and monitoring continually the measured force to determine the rate at which the portion relaxes over a period of time.

17. An apparatus for measuring quantities related to the force required to deflect along a deflection axis a portion of a resilient weatherstrip, the apparatus comprising a member defining a deflection surface, support means for receiving and positioning a strip of weatherstrip with respect to said surface such that a strip received by the support means can be oriented to extend along a longitudinal axis perpendicular to the deflection axis with an edge of the received strip running generally parallel to said longitudinal axis and to said surface, means for adjusting said support means such that said deflection surface and said edge of said received strip are in contact substantially uniformly along said longitudinal axis to an extent sufficient to cause selected deflection of a portion of said received strip substantially uniformly along said edge, a vertically mounted load cell arranged in communication with said member for detecting a vertical force component of the force, and a horizontally mounted load cell arranged in communication with said member for detecting a horizontal component of the force.

18. An apparatus for measuring the relaxation rate of the force required to deflect along a deflection axis a portion of a resilient weatherstrip, the apparatus comprising a member defining a deflection surface, support means for receiving and positioning a strip of weatherstrip with respect to said surface such that a strip received by the support means can be oriented to extend along a longitudinal axis perpendicular to the deflection axis with an edge of the received strip running generally parallel to said longitudinal axis and to said surface, means for adjusting said support means such that said deflection surface and said edge of said received strip are in contact substantially uniformly along said longitudinal axis to an extent sufficient to cause selected deflection of a portion of said received strip substantially uniformly along said edge, a vertically mounted load cell arranged in communication with said member for detecting a vertical component of the force, a horizontally mounted load cell arranged in communication with said member for detecting a horizontal component of the force, and means for continually monitoring the measured force to determine the rate at which said received strip portion relaxes over a period of time.

19. A method for measuring quantities related to the force required to deflect along a deflection axis a portion of a resilient weatherstrip, the method comprising the steps of orienting a strip of weatherstrip to extend along a longitudinal axis perpendicular to the deflection axis with an edge of the strip running generally parallel to said longitudinal axis and to a deflection surface, exerting a force on the portion with said deflection surface to cause selected deflection of the portion substantially uniformly along said edge, measuring a horizontal component of the exerted force, and measuring a vertical component of the exerted force.

20. A method for measuring the relaxation rate of a portion of a resilient weatherstrip deflected along a deflection axis, the method comprising the steps of orienting a strip of weatherstrip to extend along a longitudinal axis perpendicular to the deflection axis with an edge of the strip running generally parallel to said longitudinal axis and to a deflection surface, exerting a force on the portion with said deflection surface to cause selected deflection of the portion substantially uniformly along said edge, measuring an horizontal component of the exerted force, measuring a vertical component of the exerted force, and monitoring continually the measured force to determine the rate at which the portion relaxes over a period of time.

21. An apparatus for measuring seal recovery after deflection along a deflection axis of a portion of a resilient weatherstrip, the apparatus comprising a member defining a deflection surface which is rotatable about a pivot axis perpendicular to the deflection axis, support means for receiving and positioning a strip of weatherstrip with respect to said surface such that a strip received by the support means can be oriented to extend along a longitudinal axis perpendicular to the deflection axis and to the pivot axis with an edge of the received strip running generally parallel to said longitudinal axis and to said surface, means for adjusting said support means such that said deflection surface and said edge of said received strip are in contact substantially uniformly along said longitudinal axis to an extent sufficient to cause selected deflection of a portion of said received strip substantially uniformly along said edge, and means for indicating the displacement of said support means due to adjustment.

22. An apparatus as set forth in claim 21 further comprising means for indicating when a force is being exerted upon said deflection surface by said received strip portion.

* * * * *

UNITED STATES PATENT AND TRADEMARK OFFICE
CERTIFICATE OF CORRECTION

PATENT NO. : 5,033,308

DATED : July 23, 1991

INVENTOR(S) : Gilles Le Compagnon et al

It is certified that error appears in the above-identified patent and that said Letters Patent is hereby corrected as shown below:

On Title Page: Item [75] Inventor "David A. Ross" should read
--David A. Rose--.

Signed and Sealed this

Seventeenth Day of December, 1991

Attest:

HARRY F. MANBECK, JR.

*Attesting Officer*　　　　*Commissioner of Patents and Trademarks*